United States Patent [19]

Kung et al.

[11] Patent Number: 5,236,797
[45] Date of Patent: Aug. 17, 1993

[54] ELECTROPHOTOGRAPHIC ELEMENTS CONTAINING PHOSPHA-2,5-CYCLOHEXADIENE COMPOUNDS AS ELECTRON-TRANSPORT AGENTS

[75] Inventors: Teh-Ming Kung, Rochester; Chin H. Chen, Mendon, both of N.Y.

[73] Assignee: Eastman Kodak Company, Rochester, N.Y.

[21] Appl. No.: 895,757

[22] Filed: Jun. 9, 1992

[51] Int. Cl.$^5$ ............................................. G03G 5/047
[52] U.S. Cl. .................................. 430/58; 430/83; 430/95
[58] Field of Search ........................... 430/58, 83, 95

[56] References Cited

U.S. PATENT DOCUMENTS

| | | | |
|---|---|---|---|
| 4,514,481 | 4/1985 | Scozzafava et al. | 430/58 |
| 5,034,293 | 7/1991 | Rule et al. | 430/58 |
| 5,039,585 | 8/1991 | Rule et al. | 430/59 |

OTHER PUBLICATIONS

Märkl and Olbrich, *Angew. Chem. Internat. Ed.*, 1966, vol. 5, pp. 588–589, pp. 589–590.

*Primary Examiner*—John Goodrow
*Attorney, Agent, or Firm*—Nixon, Hargrave, Devans & Doyle

[57] ABSTRACT

Electrophotographic elements contain certain chemical compounds as electron-transport agents, which are substituted derivatives of phospha-2,5-cyclohexadiene. These compounds have good solubility or dispersibility in organic solvents and polymeric binders, and they exhibit good electron-transport properties in electrophotographic elements.

2 Claims, No Drawings

ELECTROPHOTOGRAPHIC ELEMENTS CONTAINING PHOSPHA-2,5-CYCLOHEXADIENE COMPOUNDS AS ELECTRON-TRANSPORT AGENTS

FIELD OF THE INVENTION

This invention relates to electrophotographic elements containing electron-transport agents, which are substituted derivatives of phospha-2,5-cyclohexadiene.

BACKGROUND OF THE INVENTION

In electrophotography an image comprising a pattern of electrostatic potential (also referred to as an electrostatic latent image), is formed on a surface of an electrophotographic element comprising at least an insulative photoconductive layer and an electrically conductive substrate. The electrostatic latent image is usually formed by imagewise radiation-induced discharge of a uniform potential previously formed on the surface. Typically, the electrostatic latent image is then developed into a toner image by contacting the latent image with an electrographic developer. If desired, the latent image can be transferred to another surface before development.

In latent image formation the imagewise discharge is brought about by the radiation-induced generation of electron/hole pairs, by a material (often referred to as a charge-generation material) in the electrophotographic element. Depending upon the polarity of the initially uniform electrostatic potential and the type of materials in the electrophotographic element, either the holes or the electrons that have been generated migrate toward the charged surface in the exposed areas and cause the imagewise discharge of the initial potential. What remains is a non-uniform potential constituting the electrostatic latent image.

Many electrophotographic elements are designed to be initially charged with a negative polarity. They contain material, known as a hole-transport agent, which facilitates the migration of positive holes toward the negatively charged surface in imagewise exposed areas. A positively charged toner develops the unexposed areas. Because of the wide use of negatively charging elements, many types of positively charging toners are available. Conversely, relatively few high quality negatively charging toners are available.

For some applications, however, it is desirable to develop the exposed rather than the unexposed surface areas of the element. For example, in laser printing of alphanumeric characters it is more desirable to expose the small surface area that will form visible alphanumeric toner images, rather than waste energy exposing the large background area. In order to accomplish this with available high quality positively charging toners, it is necessary to use an electrophotographic element that is designed to be positively charged. Positive toner can then develop the exposed surface areas (which will have relatively negative electrostatic potential).

An electrophotographic element designed to be initially positively charged should, however, contain an electron-transport agent, i.e., a material which facilitates the migration of photogenerated electrons toward the positively charged surface. Unfortunately, many good hole-transport agents are available, but relatively few electron transport agents are known.

A number of chemical compounds having electron-transport properties are described, for example, in U.S. Pat. Nos. 4,175,960; 4,514,481; 4,474,865; 4,559,287; 4,606,861; and 4,609,602. However, many prior art compounds have one or more drawbacks.

Some prior art electron-transport agents do not perform the electron-transporting function well under certain conditions or in certain types of electrophotographic elements. Also, some such agents cause an undesirably high rate of discharge of the electrophotographic element before it is exposed (often referred to as high dark decay).

Furthermore, some prior art electron-transport compounds have limited solubility or dispersibility in coating solvents or in polymeric binders. Attempts to include them in electrophotographic elements result in crystallization which causes problems such as undesirable dark decay, as well as scatter or absorption of actinic radiation intended to pass through the charge-transport layer.

Even when sufficient amounts of electron-transport agent can be compatibly incorporated in an electrophotographic element, problems can arise. For example, U.S. Pat. No. 4,514,481 describes a number of electron-transport agents, e.g., 4-dicyanomethylene-2,6-diphenyl-4H-thiopyran-1,1-dioxide, and illustrates incorporating them in polymeric binder layers of electrophotographic elements at a concentration of 30% by weight (based on total weight of the agent and the binder) for good performance. In fact, however, the upper limit of compatibility (solubility or homogeneous dispersibility) of compounds such as 4-dicyanomethylene-2,6-diphenyl-4H-thiopyran-1,1-dioxide in many polymeric binders is about 40% by weight. At such concentration the compounds are on the edge of incompatibility. At elevated temperatures, such as the element can encounter during normal use in a copier, the compound can more easily migrate within the binder and tend to form crystalline agglomerates.

There are additional reasons to seek electron-transport agents having improved solubility or dispersibility. For example, increasing the concentration of an electron-transport agent in a polymeric layer, in the absence of phase-separation, increases the electron-transport mobility of the layer; accordingly, photogenerated electrons move through the layer at a higher velocity and traverse the layer in a shorter period of time. The higher the mobility, the shorter is the waiting period between exposure and development, and the greater is the number of copies that can be made in a given amount of time.

Unsymmetrically substituted 2,6-diaryl-4H-thiopyran-1,1-dioxide compounds that are more readily dispersible or soluble than compounds of U.S. Pat. No. 4,514,481 are disclosed in U.S. Pat. Nos. 4,968,813, 5,013,849, 5,034,293, and 5,039,585. However, there is a continuing need for electrophotographic elements containing electron-transport agents that do not cause high dark decay and also have improved solubility or dispersibility in coating solvents and improved compatibility with polymeric binders. The compounds employed as electron-transport agents in elements of the present invention are especially soluble or dispersible and can be incorporated in polymeric binder layers at concentrations exceeding 60 weight percent.

SUMMARY OF THE INVENTION

The present invention provides electrophotographic elements containing certain chemical compounds as electron-transport agents, which are substituted derivatives of phospha-2,5-cyclohexadiene having the structure (I),

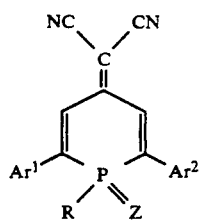

wherein Ar¹ and Ar² each independently represents an aryl group of 6 to about 10 carbon atoms, R represents an aryl, alkyl, aralkyl, or cycloalkyl group of 1 to about 10 carbon atoms, and Z is oxygen or $C(CN)_2$.

Compounds of structure (I) have unexpectedly good solubility or dispersibility in organic solvents and polymeric binders, and they exhibit good electron-transport properties in electrophotographic elements of the invention.

DETAILED DESCRIPTION OF THE INVENTION

In the phospha-2,5-cyclohexadiene compounds of structure (I), Ar¹ and Ar² are each independently aryl groups of 6 to about 10 carbon atoms, and R is an aryl, alkyl, aralkyl, or cycloalkyl group of 1 to about 10 carbon atoms. The groups can be substituted or unsubstituted. Examples of unsubstituted alkyl groups are methyl, ethyl, propyl, isopropyl, butyl, isobutyl, t-butyl, pentyl, hexyl, 2-ethylhexyl, octyl, and the like. Aralkyl groups can be benzyl, phenethyl, and the like. Cycloalkyl groups can be cyclopentyl, cyclohexyl, 4-methylcyclohexyl, and the like. For substituted alkyl and cycloalkyl groups, substituents can be alkoxy, aryloxy, and the like. For substituted aralkyl groups, substituents can be alkyl, alkoxy, halo, and the like.

In the compounds of structure (I), Z is oxygen or $C(CN)_2$.

The substituted derivatives of phospha-2,5-cyclohexadiene which are electron-transport agents in electrophotographic elements of the present invention are prepared from 1,5-diaryl-1,4-pentadien-3-ones by the following scheme:

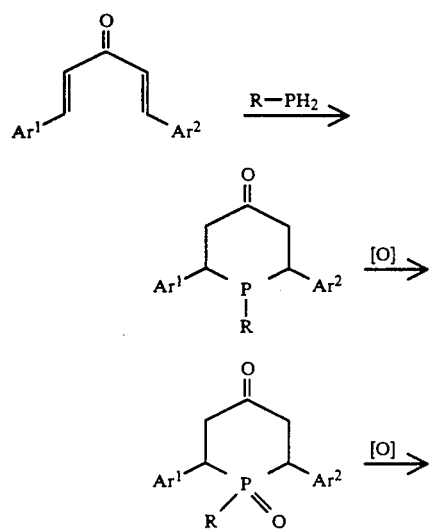

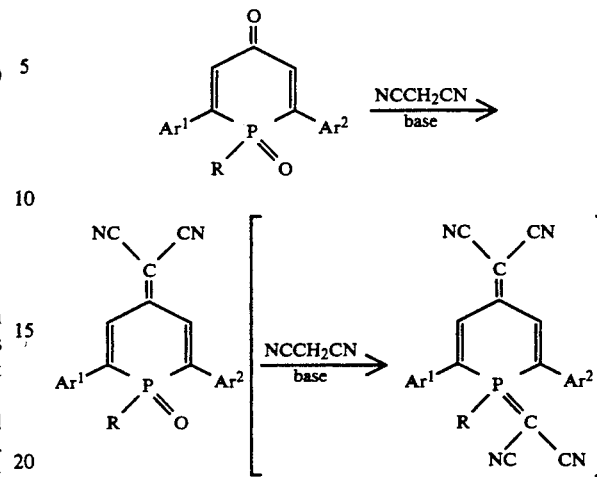

The required diarylpentadienone compounds can be synthesized as described in Scheme I and preparation A of U.S. Pat. No. 5,039,585, incorporated herein by reference. These compounds can be converted to 2,6-diarylphosphacyclohexan-4-one compounds by reaction with primary phosphines according to the procedure of Welcher and Day, *J. Org. Chem.*, 1962, Vol. 27, pp. 1824–1827.

The diarylphosphacyclohexanones can be oxidized by agents such as m-chloroperbenzoic acid to the corresponding P-oxide compounds, which can be further oxidized to 2,6-diarylphospha-2,5-cyclohexadiene-4-one P-oxides by reaction with dimethylsulfoxide in the presence of catalytic amounts of iodine and sulfuric acid. Alternatively, the 2,6-diarylphosphacyclohexadienone P-oxides can be obtained directly from the phosphacyclohexanone compounds by reaction with excess selenium dioxide in ethanol solution, as described by Markl and Olbrich, *Angew. Chem. Internat. Edit.*, 1966, Vol. 5, pp. 588–589.

Knoevenagel condensation of the phospha-2,5-cyclohexadien-4-one P-oxide compounds with malononitrile under basic conditions can be carried out by the procedure of Markl and Olbrich, ibid., pp. 589–590, or the method disclosed in U.S. Pat. No. 4,513,481, incorporated herein by reference.

The 2,6-diaryl-4-dicyanomethylene-phospha-2.5-cyclohexadiene P-oxide compounds can be converted to their P-dicyanomethylene counterparts by reaction with a second molecule of malononitrile, as described by Markl and Olbrich, op. cit., p. 589.

Shown below are formulas of new chemical compounds that are useful as electron-transport agents in electrophotographic elements of the present invention.

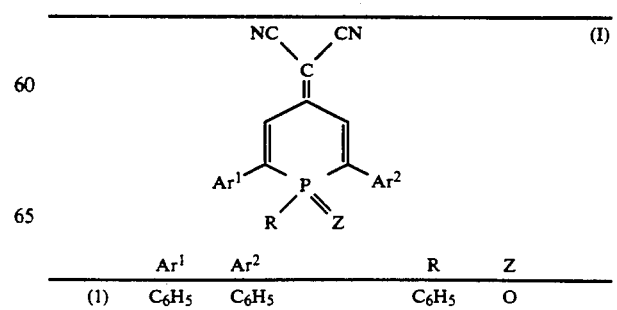

| | Ar¹ | Ar² | R | Z |
|---|---|---|---|---|
| (1) | $C_6H_5$ | $C_6H_5$ | $C_6H_5$ | O |

-continued $$\text{(I)}$$

[Structure I: central C with two CN groups (NC, CN) double-bonded to a six-membered ring containing P, with substituents Ar¹, Ar², R, and =Z on the P]

| | Ar¹ | Ar² | R | Z |
|---|---|---|---|---|
| (2) | C₆H₅ | 4-CH₃C₆H₄ | C₆H₅ | O |
| (3) | C₆H₅ | 4-C₄H₉OC₆H₄ | C₆H₅ | O |
| (4) | C₆H₅ | C₆H₅ | C₄H₉ | O |
| (5) | C₆H₅ | C₆H₅ | C₆H₁₁ | O |
| (6) | C₆H₅ | C₆H₅ | C₆H₅ | C(CN)₂ |

The new electrophotographic elements of the invention can be of various types, all of which contain one or more of the chemical compounds of structure (I) described above to serve as electron-transport agents in the elements. The various types of elements in accordance with the present invention include both those commonly referred to as single layer or single-active-layer elements and those commonly referred to as multiactive, multilayer, or multi-active-layer elements.

Single-active-layer elements are so named because they contain only one layer that is active both to generate and to transport charges in response to exposure to actinic radiation. Such elements typically comprise at least an electrically conductive layer in electrical contact with a photoconductive layer. In single-active-layer elements of the invention, the photoconductive layer contains a charge-generation material to generate electron/hole pairs in response to actinic radiation and an electron-transport material, comprising one or more of the chemical compounds of structure (I) described above, which is capable of accepting electrons generated by the charge-generation material and transporting them through the layer to effect discharge of the initially uniform electrostatic potential. The photoconductive layer is electrically insulative except when exposed to actinic radiation, and it sometimes contains an electrically insulative polymeric film-forming binder, which may itself be the charge-generating material, or it may be an additional material that is not charge-generating. In either case, the electron-transport agent is dissolved or dispersed as uniformly as possible in the binder film.

Multiactive elements are so named because they contain at least two active layers, at least one of which is capable of generating charge (i.e., electron/hole pairs) in response to exposure to actinic radiation and is therefore referred to as a charge-generation layer (CGL), and at least one of which is capable of accepting and transporting charges generated by the charge-generation layer and is therefore referred to as a charge-transport layer (CTL). Such elements typically comprise at least an electrically conductive layer, a CGL, and a CTL. Either the CGL or the CTL is in electrical contact with both the electrically conductive layer and the remaining CTL or CGL. The CGL contains at least a charge-generation material; the CTL contains at least a charge-transport agent; and either or both layers can contain an electrically insulative film-forming polymeric binder. In multiactive elements of the invention, the charge-transport agent is an electron-transport agent comprising one of the chemical compounds of structure (I) described above.

Single-active-layer and multiactive electrophotographic elements and their preparation and use in general, are well known and are described in more detail, for example, in U.S. Pat. Nos. 4,701,396; 4,666,802; 4,578,334; 4,719,163; 4,175,960; 4,514,481; and 3,615,414, the disclosures of which are incorporated herein by reference. The only essential difference of electrophotographic elements of the present invention from generally known elements is that the new elements contain chemical compounds of structure (I) as electron-transport agents.

In preparing single-active-layer electrophotographic elements of the invention, the components of the photoconductive layer, including any desired addenda, can be dissolved or dispersed together in a liquid and can be coated on an electrically conductive layer, or support. The liquid is then allowed or caused to evaporate from the mixture to form the permanent layer, which contains from about 10 to about 70 weight percent of the electron-transport agent and from 0.01 to about 50 weight percent of the charge-generating material. Included among many useful liquids for this purpose are, for example, aromatic hydrocarbons such as benzene, toluene, xylene and mesitylene; ketones such as acetone and butanone; halogenated hydrocarbons such as dichloromethane, trichloroethane, chloroform, and ethylene chloride; ethers, including ethyl ether and cyclic ethers such as tetrahydrofuran; other solvents such as acetonitrile and dimethylsulfoxide; and mixtures thereof.

In preparing multiactive electrophotographic elements of the invention, the components of the CTL can be similarly dissolved or dispersed in such a liquid coating vehicle and can be coated on either an electrically conductive layer or support, or on a CGL previously similarly coated or otherwise formed on the conductive layer or support. In the former case, a CGL is thereafter coated or otherwise formed (e.g., by vacuum-deposition) on the CTL. The CTL will usually contain from about 10 to about 70 weight percent of the electron-transport agent, although concentrations outside that range may be found to be useful in some cases.

Various electrically conductive layers or supports can be employed in electrophotographic elements of the invention, for example, paper (at a relative humidity above 20 percent); aluminum-paper laminates; metal foils such as aluminum foil, zinc foil, etc.; metal plates such as aluminum, copper, zinc, brass and galvanized plates; vapor deposited metal layers such as silver, chromium, vanadium, gold, nickel, aluminum and the like; and semiconductive layers such as cuprous iodide and indium tin oxide. The metal or semiconductive layers can be coated on paper or conventional photographic film bases such as poly(ethylene terephthalate), cellulose acetate, polystyrene, etc. Such conducting materials as chromium, nickel, etc. can be vacuum-deposited on transparent film supports in sufficiently thin layers to allow electrophotographic elements so prepared to be exposed from either side.

Any charge-generation material can be utilized in elements of the invention. Such materials include inorganic and organic (including monomeric organic, metallo-organic and polymeric organic) materials, for example, zinc oxide, lead oxide, selenium, or phthalocyanine, perylene, arylamine, polyarylalkane, and polycarbazole materials, among many others.

In solvent-coating a photoconductive layer of a single-active-layer element or a CGL and/or CTL of a multiactive element of the invention, a film-forming polymeric binder can be employed. The binder may, if it is electrically insultating, help provide the element with electrically insulating characteristics. It also is useful in coating the layer, in adhering the layer to an adjacent layer, and, when it is a top layer, in providing a smooth, easy to clean, wear-resistant surface.

The optimum ratio of charge-generation or charge-transport material to binder may vary widely, depending on the particular materials employed. In general, useful results are obtained when the amount of active charge-generation and/or charge-transport material contained within the layer is within the range of from about 0.01 to about 90 weight percent, based on the dry weight of the layer.

Representative materials which can be employed as binders in charge-generation and charge-transport layers are film-forming polymers having a fairly high dielectric strength and good electrically insulating properties. Such binders include, for example, styrene-butadiene copolymers; vinyltoluene-styrene copolymers; styrene-alkyd resins; silicone-alkyd resins; soya-alkyd resins; vinylidene chloride-vinyl chloride copolymers; poly(vinylidene chloride); vinylidene chloride-acrylonitrile copolymers; vinyl acetate-vinyl chloride copolymers; poly(vinyl acetals), such as poly(vinyl butyral); nitrated polystyrene; poly(methylstyrene); isobutylene polymers; polyesters, such as poly[ethylene-co-alkylenebis(alkyleneoxyaryl)phenylenedicarboxylate]; phenol-formaldehyde resins; ketone resins; polyamides; polycarbonates; polythiocarbonates; poly[ethylene-co-isopropylidene-2,2-bis(ethyleneoxyphenylene)terephthalate]; copolymers of vinyl haloacrylates and vinyl acetate; chlorinated polyolefins such as chlorinated polyethylene; and polyimides, such as poly[1,1,3-trimethyl-3-(4'-phenyl)-5-indane pyromellitimide].

Binder polymers should provide little or no interference with the generation or transport of charges in the layer. Examples of binder polymers which are especially useful include bisphenol A polycarbonates and polyesters such as poly[(4,4'-norbornylidene)diphenylene terephthalate-co-azelate].

CGL's and CTL's in elements of the invention can also optionally contain other addenda such as leveling agents, surfactants, plasticizers, sensitizers, contrast-control agents, and release agents, as is well known in the art.

Also, elements of the invention can contain any of the optional additional layers known to be useful in electrophotographic elements in general, for example, subbing layers, overcoat layers, barrier layers, and screening layers.

The following preparations and examples are presented to further illustrate some specific electrophotographic elements of the invention and chemical compounds useful as electron-transport agents therein.

EXAMPLE 1

Preparation of
4-dicyanomethylene-1,2,6-triphenylphospha-2,5-cyclohexadiene P-oxide The procedures given below are representative of those that can be used to prepare the electron-transport agents employed in electrophotographic elements of the present invention.

Following the procedure of Welcher and Day, *J. Org. Chem.*, 1962, Vol. 27, pp. 1824–1827, 66 g of crude 1,2,6-triphenyl-phosphacyclohexan-4-one was prepared from 53 g (0.226 mole) of 1,5-diphenyl-1,4-pentadien-3-one and 25 g (0.227 mole) of phenylphosphine.

To a dichloromethane (100 ml) solution of 2.3 g (0.0067 mole) of the phosphacyclohexanone compound prepared as described above was added 1.4 g (0.0081 mole) of m-chloroperbenzoic acid. The mixture was stirred until complete solution occurred, then allowed to stand overnight while the solvent evaporated. The residue was washed with dilute aqueous sodium bicarbonate, collected, washed with water, and dried to give 1,2,6-triphenylphosphacyclohexan-4-one P-oxide in practically quantitative yield.

A mixture of 2.0 g (0.0056 mole) of the phosphacyclohexanone P-oxide compound prepared as described above, 25 ml of dimethylsulfoxide, 0.5 ml of concentrated sulfuric acid, and a catalytic amount of iodine was heated for 15 hours at 110° C., then cooled, and poured into water. The precipitate was collected, washed with water, dried, dissolved in a small volume of dichloromethane, and flash chromatographed on a short silica gel column, with elution by 1:3 ethyl acetate:hexane. There was obtained 1.25 g (63% yield) of 1,2,6-triphenylphospha-2,5-cyclohexadien-4-one P-oxide, whose structure was confirmed by $^1$HNMR, IR, and field desorption mass spectral (FDMS) analyses.

To a mixture of 0.25 g of 1,2,6-triphenylphospha-2,5-cyclohexadien-4-one P-oxide and 0.060 g of malononitrile in 100 ml of ethanol was added 1 drop of piperidine. The red mixture was heated on a steam bath for about one hour, then allowed to cool to room temperature overnight. The product crystallized as dark greenish brown metallic needles. It was collected and dried to give 0.247 g of 4-dicyanomethylene-1,2,6-triphenylphospha-2,5-cyclohexadiene P-oxide, whose structure was confirmed by $^1$HNMR and FDMS analyses.

The structure, preparation, and measurement of performance of electrophotographic elements within the scope of the invention are described below. Electrophotographic sensitivity of the elements of the invention was demonstrated by electrostatically corona-charging them to an initial positive potential, then exposing them to actinic radiation (radiation having peak intensity at a wavelength to which the charge-generation material in the elements are sensitive in order to generate electron-hole pairs) in amounts sufficient to discharge 50% and 80% of the initial voltage. Electrophotographic sensitivity was measured in terms of the amount of incident actinic radiant energy (expressed in ergs/cm$^2$) needed to discharge the initial voltage down to the desired level. The lower the amount of radiation needed to achieve the desired degree of discharge, the higher is the electrophotographic sensitivity of the element, and vice versa.

In illustrating dark decay properties, the rate of dissipation of the initial voltage, expressed in volts/second (V/s), was measured while the elements remained in darkness, i.e., before any exposure to actinic radiation. This was accomplished by measuring the initial voltage and the voltage remaining in the element after 2 seconds in darkness and dividing the difference by 2. The lower the rate of discharge in darkness, the better is the dark decay property of the elements, i.e., the better their ability to retain their initial potential before exposure.

In the tables of performance data in the following examples, "Electron-transport agent" refers to the chemical compound incorporated in the CTL of an electrophotographic element to serve as an electron-transport agent. "Wt. %" refers to the percent by weight of electron-transport agent employed, based on the total weight of polymeric binder and electron-transport agent included in the solution used to coat the CTL of the element. "$V_o$" refers to the uniform positive potential in volts on the surface of the elements, after they were charged by corona-charging and after any dark decay, such potential having been measured just prior to any exposure of the elements to actinic radiation. "DD" refers to the rate of dark decay of the elements, prior to exposure to actinic radiation, measured in volts/second (V/s) as described above.

Electrons generated in the CGL in proportion to the amount of incident actinic radiant energy migrate to the charged surface of the element and discharge it. "E ($V_o$ 50%)" refers to the amount of incident actinic radiant energy, expressed in ergs/cm$^2$, needed to discharge 50% of $V_o$. "E ($V_o$ 80%)" refers to the amount of actinic radiant energy needed to discharge 80% of $V_o$.

EXAMPLE 2

Structure, Preparation, and Performance of Electrophotographic Elements

An electrophotographic element of the invention containing a new electron-transport agent in its CTL was prepared as described below.

A thin conductive layer of aluminum was vacuum-deposited on a 178 mm thick film of polyethylene terephthalate.

A charge-generation layer (CGL) was prepared by dispersing 2 parts by weight of titanyl tetrafluorophthalocyanine (described in U.S. Pat. No. 4,701,396), a charge-generation material, in a solution of 1 part by weight of a polymeric binder, comprising a polyester formed from 4,4'-(2-norbomylidene)diphenol and terephthalic acid: azelaic acid (40:60 molar ratio) in dichloromethane, ball milling the dispersion for 60 hours, diluting with a mixture of dichloromethane and 1,1,2-trichloroethane (final weight ratio of dichloromethane; trichloroethane was 80:20) to achieve suitable coating viscosity, coating the dispersion on the conductive layer, and evaporating the solvent to yield a CGL of about 0.5 μm thickness.

A coating solution for forming a charge-transport layer (CTL) comprising 10 weight percent solids in dichloromethane was then prepared. The solids comprised the electron-transport agent, a substituted phospha-2,5-cyclohexadiene compound prepared as described in Example 1 above, and a polymeric binder comprising a polyester formed from 4,4'-(2-norbornylidene) diphenol and terephthalic acid:azelaic acid (40:60 molar ratio). The concentration of electron-transport agents was as noted in Table I. The solution was then coated on the conductive support containing the CGL to form the CTL on the CGL. The combined thickness of the CGL and CTL was about 10 μm.

Control coatings were prepared and coated in the same manner, using the following electron-transport agents, which are not of the invention:

(a) 4-dicyanomethylene-2,6-diphenyl-4H-thiopyran-1,1-dioxide (compound 3 of Table I of U.S. Pat. No. 4,514,481.

(b) 4-dicyanomethylene-2-phenyl-6-(4-tolyl)-4H-thiopyran-1,1-dioxide (Compound I-A of U.S. Pat. No. 5,039,585).

Each of the electrophotographic elements so prepared was corona-charged to a uniform positive potential.

Dark decay rate of the initial potential was measured for each element.

Each of the uniformly charged elements was subjected to simulated imaging exposure by exposing it at a rate of about 3 ergs per cm$^2$ of element surface per second through the outer surface of the CTL to radiation at a wavelength of about 820 nm, then determining the values for E($V_o$ 50%) and E($V_o$ 80%).

The results are presented in Table I.

TABLE I

| Example | Electron-transport agent | Wt. % | Vo (V) | DD (V/s) | E (V$_o$ 50%) (ergs/cm$^2$) |
|---|---|---|---|---|---|
| Control (a) | 4-dicyanomethylene-2,6-diphenyl-4H-thiopyran-1,1 dioxide | 30 | 306 | 2 | 5.6 |
| Control (b) | 4-dicyanomethylene-2-phenyl-6-(4-tolyl)-4H-thiopyran-1,1 dioxide | 40 | 294 | 1 | 5.0 |
| Compound (1) | 4-dicyanomethylene 1,2,6-triphenyl-phospha-2,5-cyclo-hexadiene P-oxide | 45 | 308 | 0 | 9.0 |

The data in Table I show that compound (1) functions as an electron-transport agent in an electrophotographic element of the invention, with dark decay properties similar to those shown by electron-transport agents of the prior art. The data also illustrate the very good solubility or dispersibility properties of compound (1), which enabled it to be incorporated at a concentration of 45 weight percent in the CTL binder polymer.

EXAMPLE 3

Preparation and Performance of Electrophotographic Elements with Varying CGL Layers A series of electrophotographic elements containing compound (1) as an electron-transport agent but with varying CGL layers was prepared. For element 1, an aluminum-coated polyethylene terephthalate support, prepared as described in Example 2, was overcoated by electron-beam evaporation with a 500 angstrom-thick layer of silicon dioxide prior to application of a CGL containing titanyl tetrafluorophthalocyanine, also prepared as described in Example 2.

For element 2, a polyethylene terephthalate support coated with aluminum and silicon dioxide layers as described above was overcoated with a CGL of about 0.3 μm thickness, applied by sublimation of bromoindiumphthalocyanine (described in U.S. Pat. Nos. 4,666,802 and 4,727,139). The layer of sublimed bromoindiumphthalocyanine was converted from an amorphous to a crystalline state by overcoating it with 1,1,2-trichloroethane, then drying for 30 minutes at 110° C.

For element 3, a thin conductive layer of nickel was vacuum-deposited on a polyethylene terephthalate support. A 0.3 μm-thick CGL was then applied by vacuum deposition of selenium pellets.

Each of the CGLs prepared as described above were overcoated, using a 5-mil (125 μm) doctor blade, with a dichloromethane solution containing 10% solids, comprising a mixture of the electron-transport agent compound (1) and the polyester from 4,4'-(2-norbornylidene)-diphenol and terephthalic acid:azelaic acid (40:60 molar ratio). The CTLs so applied were about 10 μm thick and contained 45 weight percent compound (1) and 55 weight percent polymeric binder. The coatings containing the CTL over the CGL were heated in an oven at 70° C. for 30 minutes before being uniformly corona charged to a positive potential.

Each of the uniformly charged elements was subjected to simulated imaging exposure by exposing it to radiation at a rate of about 3 ergs per cm$^2$ of element surface per second through the outer surface of the CTL, then measuring the values for E(V$_o$ 50%) and E(V$_o$ 80%).

The results are shown in Table II.

TABLE II

| Element | Material in CGL | Radiation Wavelength (nm) | Vo (V) | DD (V/s) | E (V$_o$ 50%) (ergs/cm$^2$) | E (V$_o$ 80%) (ergs/cm$^2$) |
|---|---|---|---|---|---|---|
| 1 | titanyl tetrafluorophthalocyanine | 830 | 305 | 1 | 5.7 | 15.9 |
| 2 | bromoindiumphthalocyanine | 780 | 300 | 30 | 6.6 | 18.9 |
| 3 | selenium | 500 | 300 | 0 | 15 | 31.2 |

As shown by the data in Table II, elements 1 and 2 of the invention, which contained titanyl tetrafluorophthalocyanine and bromoindiumphthalocyanine, respectively, in the CGL, exhibited similar good electrophotographic sensitivity, although dark decay characteristics of the former element were better than those of the latter. Element 3, which contained selenium in the CGL was less sensitive than elements 1 and 2, but its dark decay properties were good. Thus, the results in Table II illustrate that compound (1) can be incorporated in the CTL at a concentration of 45 weight percent and functions as an electron-transport agent in electrophotographic elements of the invention having charge-generation layers of varying structure and composition.

The invention has been described in detail with particular reference to certain preferred embodiments thereof, but it should be appreciated that variations and modifications can be effected within the spirit and scope of the invention.

What is claimed is:

1. In an electrophotographic element comprising:
    an electrically conductive layer; a charge-generation layer comprising a charge-generating material; and a charge-transport layer comprising a polymeric film containing an electron-transport agent,
    the improvement wherein the electron-transport agent comprises a chemical compound having the structure

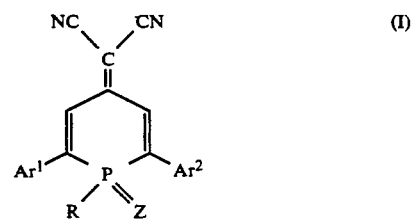

(I)

wherein Ar$^1$ and Ar$^2$ each independently represents an aryl group of 6 to about 10 carbon atoms, R represents an aryl, alkyl, aralkyl, or cycloalkyl group of 1 to about 10 carbon atoms, and Z is oxygen or C(CN)$_2$.

2. The electrophotographic element of claim 1, wherein Ar$^1$, Ar$^2$, and R are phenyl, and Z is oxygen.

* * * * *